/

US010405527B2

(12) United States Patent
Li et al.

(10) Patent No.: US 10,405,527 B2
(45) Date of Patent: Sep. 10, 2019

(54) METHOD AND SYSTEM OF CULTIVATING CORDYCEPS

(71) Applicants: Sunshine Lake Pharma Co., Ltd., Dongguan, Guangdong (CN); Yichang Shanchengshuidu Cordyceps Co., LTD., Yidu, Yichang, Hubei (CN)

(72) Inventors: Wenjia Li, Dongguan (CN); Zongyao Zhang, Dongguan (CN); Quanping Li, Dongguan (CN); Yanhua Lv, Dongguan (CN); Zhengming Qian, Dongguan (CN)

(73) Assignees: SUNSHINE LAKE PHARMA CO., LTD, Dongguan, Guangdong (CN); YICHANG SHANCHENGSHUIDU CORDYCEPS CO., LTD., Yichang, Hubei Province (CN)

( * ) Notice: Subject to any disclaimer, the term of this patent is extended or adjusted under 35 U.S.C. 154(b) by 512 days.

(21) Appl. No.: 15/365,969

(22) Filed: Dec. 1, 2016

(65) Prior Publication Data
US 2017/0273250 A1   Sep. 28, 2017

(30) Foreign Application Priority Data

Mar. 22, 2016   (CN) .......................... 2016 1 0167983
Apr. 22, 2016   (CN) .......................... 2016 1 0261457

(51) Int. Cl.
*A01K 67/00*   (2006.01)
*A01K 67/033*   (2006.01)
(Continued)

(52) U.S. Cl.
CPC ............ *A01K 67/033* (2013.01); *A01G 18/00* (2018.02); *A01M 1/04* (2013.01); *A01M 1/106* (2013.01);
(Continued)

(58) Field of Classification Search
CPC ...... A01K 67/033; A01K 67/00; A01G 18/00; A01M 1/04
See application file for complete search history.

(56) References Cited

FOREIGN PATENT DOCUMENTS

| CN | 1560228 A | 1/2005 |
|----|-----------|--------|
| CN | 1948456 A | 4/2007 |

(Continued)

OTHER PUBLICATIONS

ISR of PCT/CN2016/108498.

*Primary Examiner* — Monica L Williams
*Assistant Examiner* — Aaron M Rodziwicz
(74) *Attorney, Agent, or Firm* — Kam Wah Law

(57) ABSTRACT

The present invention relates to a system and method of cultivating *Cordyceps*, specifically, provided herein is a system of cultivating *Cordyceps* comprising: a *Hepialus* moth trapping device; a *Hepialus* moth eggs screening device, wherein the device is connected with the *Hepialus* moth trapping device; an ascospores-collecting device; a mycelia-preparing device; a conidia-preparing device; an infection device, wherein the device is connected with the ascospores-collecting device, the mycelia-preparing device and the conidia-preparing device; and a feeding device, wherein the device is connected with the *Hepialus* moth eggs screening device and the infection device. And also provided is a method of using the system to cultivate *Cordyceps*.

18 Claims, 8 Drawing Sheets

(51) Int. Cl.
*A01M 1/04* (2006.01)
*A01M 1/10* (2006.01)
*F21V 23/00* (2015.01)
*A01G 18/00* (2018.01)
*C12N 1/14* (2006.01)
*F21Y 113/10* (2016.01)
*F21Y 115/10* (2016.01)

(52) U.S. Cl.
CPC .............. *C12N 1/14* (2013.01); *F21V 23/003* (2013.01); *F21Y 2113/10* (2016.08); *F21Y 2115/10* (2016.08)

(56) References Cited

FOREIGN PATENT DOCUMENTS

| | | | |
|---|---|---|---|
| CN | 102106235 A | 6/2011 | |
| CN | 102696555 A | 10/2012 | |
| CN | 102792855 A | 11/2012 | |
| CN | 102960183 A | 3/2013 | |
| CN | 103299963 A | 9/2013 | |
| CN | 103314786 A | 9/2013 | |
| CN | 103355257 A | 10/2013 | |
| CN | 103548779 A | 2/2014 | |
| CN | 103858669 A | 6/2014 | |
| CN | 103861816 A | 6/2014 | |
| CN | 103877127 A | 6/2014 | |
| CN | 104365319 A | 2/2015 | |
| CN | 104920066 | 9/2015 | |
| CN | 105028335 A | 11/2015 | |
| EP | 1275710 A1 | 2/2003 | |
| KR | 20120049795 A | 6/2012 | |
| WO | WO-02065836 A2 * | 8/2002 | ............. A01N 63/04 |

\* cited by examiner

METHOD AND SYSTEM OF CULTIVATING CORDYCEPS

CROSS-REFERENCE TO RELATED APPLICATION

This application claims priority to Chinese Patent Serial No. 201610167983.7, filed on Mar. 22, 2016, and Chinese Patent Serial No. 201610261457.7, filed on Apr. 22, 2016, both of which are hereby incorporated by reference in their entirety.

FIELD OF THE INVENTION

The present invention refers to the field of biotechnology, specifically to a method and system of cultivating *Cordyceps*.

BACKGROUND OF THE INVENTION

*Cordyceps* is endemic to China, which is an rare traditional Chinese medicine and distributed mainly in Tibet, Qinghai, Sichuan, Yunnan and Gansu provinces; *Cordyceps* is an entomogenous ascus fungus, exactly a parasitic fungus *Cordyceps* bat moth larvae in the body of the sub-Block and larval body complex, which belongs to *Cordyceps* (Frey) Link, Clavicipitaceae, Hypocreales, Sordariomycetidae, Ascomycetcs, Ascomycota, Fungi. The growth conditions of *Cordyceps* are very strict, which correlate closely to altitude, vegetation and climate, etc.

*Cordyceps* contains various active ingredients, including water, *Cordyceps* polysaccharide, crude protein, crude fiber and amino acid, etc. *Cordyceps* has various pharmacological effects, and also has antibechic, expectorant, antiphlogistic, anti-cornea transplant rejection, anti-stress, anti-aging, antibacterial, antiviral and antineoplastic effects, etc.

Recently, the yield of *Cordyceps* decreased significantly because of degradation of ecological environment and overexploitation, and also *Cordyceps* have decreased in size and declined in quality.

Therefore, a system and method of cultivating *Cordyceps* artificially and industrially become a pressing need.

SUMMARY OF THE INVENTION

In a first aspect, the present invention provides a system of cultivating *Cordyceps*, which has advantages of operations with less manual intervention, suitability of industrial production of *Cordyceps*, and steady production and high quality of *Cordyceps* obtained by cultivating. In a second aspect, the present invention also provides a method of using the system of cultivating *Cordyceps*.

According to the first aspect of the invention, the system of cultivating *Cordyceps* provided herein comprises a *Hepialus* moth trapping device, wherein the *Hepialus* moth trapping device is used for trapping *Hepialus* moth and collecting *Hepialus* moth eggs; a *Hepialus* moth eggs screening device, wherein the *Hepialus* moth eggs screening device is connected with the *Hepialus* moth trapping device, and wherein the *Hepialus* moth eggs screening device is used for screening the *Hepialus* moth eggs automatically and collecting the screened *Hepialus* moth eggs quantificationally; an ascospores-collecting device, wherein the ascospores-collecting device is used for collecting ascospores of *Cordyceps*; a mycelia-preparing device, wherein the mycelia-preparing device is used in liquid fermentation of *Hirsutella sinensis* to obtain mycelia thereof; a conidia-preparing device, wherein the conidia-preparing device is used in solid fermentation of *Hirsutella sinensis* to obtain conidia thereof; an infection device, wherein the infection device is connected with the ascospores-collecting device, the mycelia-preparing device and the conidia-preparing device, and wherein the infection device is used for infecting *Hepialus* moth larvae with infective liquid; and wherein the infective liquid contains *Cordyceps* ascospores, *Hirsutella sinensis* conidia and *Hirsutella sinensis* mycelia; and a feeding device, wherein the feeding device is connected with the *Hepialus* moth eggs screening device and the infecting device, and wherein the feeding device is used for incubating the screened *Hepialus* moth eggs and incubating the infected *Hepialus* moth larvae to obtain *Cordyceps*. The present invention provides a full system of cultivating *Cordyceps* artificially from initial trapping to output of *Cordyceps*, which can realize controllable yield and quality, and avoid the problems that the yield of *Cordyceps* decreases significantly, and the size of *Cordyceps* decreases and the quality declines, owing to degradation of ecological environment and overexploitation; meanwhile, the system can realize industrial production.

In some embodiments, the *Hepialus* moth trapping device comprises a first body, wherein a *Hepialus* moth trapping space is limited in the first body; a moth trapping platform, wherein the moth trapping platform is installed outside the first body; and a non-specific attracting light source and a specific attracting light source, wherein the non-specific attracting light source and the specific attracting light source are installed successively along the direction of the moth trapping platform to the *Hepialus* moth trapping space. The *Hepialus* moth trapping device further reduces manual intervention in the system of cultivating *Cordyceps* disclosed herein. The inventors discovered, surprisingly, that there is a difference in phototaxis between *Hepialus* moth and other winged insects based on a long-term in-depth research in *Hepialus* moth, specifically, *Hepialus* moth is sensitive to both the red light and black light, but other winged insects are sensitive to the black light and insensitive to the red light, and when *Hepialus* moths are absorbed by the black light, they merely flap wings but do not mate. Based on the above discovery, the inventors installed a light of specific wavelengths in specific area of the *Hepialus* moth trapping device in order to eliminate interference from other winged insects and absorb specifically *Hepialus* moth to mate and oviposit in the specific area. Thus it can be seen that the inventors obtained the *Hepialus* moth trapping device through costing a lot of creative works, the device can eliminate interference from other winged insects and absorb specifically *Hepialus* moth to mate and oviposit in the specific area.

In some embodiments, the *Hepialus* moth trapping device further comprises a *Hepialus* moth crawling board, wherein the *Hepialus* moth crawling board is connected with the moth trapping platform at one end, and the other end is connected with the first body; the non-specific attracting light source is a black light lamp, wherein the black light lamp is installed over the moth trapping platform; the specific attracting light source is a red light lamp, wherein the red light lamp is installed over the first body; a controller, wherein the controller is connected with the black light lamp and the red light lamp respectively; and which is used for controlling the bright and dim light of each lamp. Preferably, "one end" is opposite to "the other end". Preferably, there are gauzes installed on the inside surface of the first body except the upper surface and the right surface in the above *Hepialus* moth trapping device, and the gauze of the first body is used to attach *Hepialus* moth. Preferably, there are visors installed on the front surface, rear surface and left surface of the above *Hepialus* moth trapping device.

In some specific embodiments, the first body comprises a partition in the inner side, wherein the first body is divided into a *Hepialus* moth trapping area and a *Hepialus* moth ovipositing area by the partition, and the *Hepialus* moth trapping area and the *Hepialus* moth ovipositing area open onto each other at the bottom of the partition, and wherein the *Hepialus* moth trapping area is connected with the moth trapping platform through the *Hepialus* moth crawling board.

In some embodiments, the wavelength of the black light is from 330 to 400 nm; preferably, it is 350 nm.

In some embodiments, the red light lamps comprises a first red light lamp and a second red light lamp, wherein the first red light lamp is installed over the junction of the *Hepialus* moth crawling board and the *Hepialus* moth trapping area; and wherein the second red light lamp is installed over the junction of the *Hepialus* moth trapping area and the *Hepialus* moth ovipositing area, and under the bottom of the partition.

In some embodiments, the wavelength of the red light is from 600 to 700 nm; preferably, it is 620 nm.

In some embodiments, the *Hepialus* moth trapping device further comprises one or more LED blue light lamps and an *Hepialus* moth eggs collecting groove, wherein the LED blue light lamp is installed in the *Hepialus* moth ovipositing area, the *Hepialus* moth eggs collecting groove is installed under the first body. Preferably, the *Hepialus* moth eggs collecting groove is equipped with one or more drainage holes.

In some specific embodiments, the LED blue light lamp has an illumination of 25~35 lux, preferably of 30 lux. The *Hepialus* moth is more likely to mate and oviposit in this blue light.

In some specific embodiments, the *Hepialus* moth trapping device further comprises a rainproof shelter, and wherein the rainproof shelter is installed over the first body.

By using the *Hepialus* moth trapping device, multi functions, such as trapping moth, mating, oviposition and collecting eggs, etc., can be realized at the same time; owing to each setting being suited for growth behavior of *Hepialus* moth perfectly, the *Hepialus* moth oviposits at an optimum environment, the egg number is largest and the moth eggs have a best quality. In addition, by using the above *Hepialus* moth trapping device, the interference from other winged insects can be eliminated; meanwhile, the rainproof shelter and the drainage holes can be installed to solve multi technological problems when trapping moth outdoors, such as severe weather.

The collected *Hepialus* moth eggs are of all sizes, some too small *Hepialus* moth eggs are hatched to produce small *Cordyceps* due to undernutrition, which can influence the overall quality of *Cordyceps*, otherwise, some developmental retardation and immature eggs can lead to a low hatch rate; therefore, a screening of eggs is necessary before incubation, several million or several hundred million of *Hepialus* moth eggs are needed in each large scale cultivation of *Cordyceps*, so the screening efficiency is required urgently to raise.

There are eggs holes and color sensors installed in the *Hepialus* moth eggs screening device of the invention, therefore specific size and matured *Hepialus* moth eggs can be obtained through screening.

In some embodiments, the *Hepialus* moth eggs screening device comprises a dispersing box, wherein the dispersing box is an input port for importing eggs to be screened; one or more dropping channels, wherein the dropping channel is connected with the dispersing box at one end; one or more selecting channels, wherein the selecting channel is connected at the other end of the dropping channel, and wherein an extra small eggs hole, a color sensor, a gas valve and a mature eggs collecting device are set up on the selecting channel successively.

In some embodiments, the selecting channel further comprises an eggs hole, wherein the eggs hole is set up on the selecting channel and located downstream from the extra small eggs hole, and wherein the bore diameter of the eggs hole is larger than that of the extra small eggs hole; multiple sub-selecting channels, wherein the sub-selecting channels are connected with the selecting channel through the eggs hole; the color sensor is set up on the sub-selecting channel and located downstream from the eggs hole; the gas valve is set up on the sub-selecting channel and located downstream from the color sensor, and the gas valve is used for blowing immature eggs away; the mature eggs collecting device is located on the sub-selecting channel at the far end from the selecting channel, and the mature eggs collecting device is used for collecting matured *Hepialus* moth eggs.

In some specific embodiments, the dispersing box comprises multiple dispersing grids, wherein the dispersing grids are connected with dropping channel, and the dropping channel is setup obliquely. Thus it is better for delivering *Hepialus* moth eggs.

In some specific embodiments, the *Hepialus* moth eggs screening device further comprises a flicking eggs device, and wherein the flicking eggs device is installed in the center of the dispersing box, when the *Hepialus* moth egg drops on the flicking eggs device, the *Hepialus* moth egg is flicked to the dispersing grids.

In some specific embodiments, the *Hepialus* moth eggs screening device further comprises a pouring eggs device, and wherein the pouring eggs device is installed over the flicking eggs device. Preferably, the pouring eggs device is funnel-shaped.

According to the specific embodiments of the selecting channels and the sub-selecting channels are set up obliquely. Thus it is better for delivering *Hepialus* moth eggs.

In some specific embodiments, the extra small eggs hole and/or the eggs hole may be one or multiple, and the bore diameter of the extra small eggs hole and/or the eggs hole may be adjusted according to the actual requirements, preferably, the bore diameter of the extra small eggs hole is 0.55±0.1 mm; the bore diameter of the eggs hole is 1.2±0.2 mm.

In some specific embodiments, the *Hepialus* moth eggs screening device further comprises a extra small eggs collecting device, the extra small eggs collecting device is connected to the extra small eggs hole.

In some specific embodiments, the *Hepialus* moth eggs screening device further comprises an immature eggs collecting device, and the immature eggs collecting device is installed at the side opposite to the gas valve, which is used for collecting developmental retardation and immature eggs.

In some specific embodiments, the *Hepialus* moth eggs screening device further comprises a counter, wherein the counter is set up on the selecting channel and located downstream from the gas valve, and which is used for quantificationally collecting the screened *Hepialus* moth eggs.

The freshly laid *Hepialus* moth egg is white, the color would become black with the maturation of the *Hepialus* moth egg; the inventors discovered unexpectedly that the color sensor can be used in selecting out the developmental retardation eggs based on the above discovery, thus the *Hepialus* moth eggs screening device is produced. Furthermore, conventional sprinkling eggs process comprises quantifying eggs by using a spoon, but there is a tiny deviation between each spoon, and the process can not guarantee that sprinkled eggs are at an optimum quantity. The *Hepialus* moth eggs screening device of the present invention comprises a counter, which can realize accurate sprinkling eggs, and the quantity of the sprinkled eggs is calculated exactly to fit cultured space and the feed quantity, which can reach maximum capacity of this step and increase *Cordyceps* output.

The above *Hepialus* moth eggs screening device can screen out the small eggs though the extra small eggs hole, and remove the developmental retardation and immature eggs by using the color sensor to distinguish the development of the *Hepialus* moth eggs, the last collected eggs are large and mature, thereby a high hatching rate is ensured.

In some embodiments, the ascospores-collecting device comprises: a barrel, wherein an ascospores collecting space is limited in the barrel, wherein the barrel has an open top; a closable opening, wherein the closable opening is installed in the bottom of the barrel, optionally, a protrusion of the closable opening is higher than the bottom of the barrel; a cover panel, wherein the cover panel is installed over the top of the barrel, and wherein the cover panel is connected with the barrel through a support; a turnable shaft, wherein the turnable shaft passes through the cover panel; a wind-power collecting device, wherein the wind-power collecting device is connected to the far end of the turnable shaft from the barrel; a fan, wherein the fan is connected to the other end of the turnable shaft which is close to the barrel.

In the prior art, the action of collecting *Cordyceps* ascospores is merely carried out under an invariable temperature in a lab, meanwhile the ascospores have a limited number and the quality of which can not be guaranteed; however by using the ascospores-collecting device of the present invention, the action of collecting *Cordyceps* ascospores can be carried out in the wild, and the collected *Cordyceps* ascospores are wild ascospores having high vigor and original characteristics, and therefore the quality and quantity of *Cordyceps* can be ensured.

In some embodiments, the infecting device comprises a mesh frame; and one or more raised portions, wherein the raised portion is formed on the mesh frame.

In some specific embodiments, the mesh frame is collapsible.

The infecting device can be used for further promoting *Hepialus* moth larvae infection with the infective liquid.

In some embodiments, the feeding device comprises a second body, wherein a feeding space is limited in the second body; a water compensating pipeline, wherein the water compensating pipeline is installed at the bottom of the feeding space, wherein the water compensating pipeline comprises one collective pipeline and multiple sub pipelines; wherein the collective pipeline is connected with the sub pipeline, and wherein the collective pipeline has a water inlet, and the sub pipeline has a water outlet and multiple water outlet holes on the wall; and a temperature control device, wherein the temperature control device is installed at the bottom of the feeding space, and wherein which is used for controlling the temperature of the feeding space.

In some specific embodiments, the cross sectional area of the feeding space defined in the second body is gradually increased from bottom to top.

The feeding device has the following advantages:

(1) The cross sectional area of the feeding space is gradually increased from bottom to top, which can realize transition from small space needed by small worm to lager space needed by big worm, and economize the initial fodder and matrix;

(2) *Hepialus* moth larvae live in deep soil at most time, the water compensating pipeline is installed in the bottom of the feeding device, water is supplemented from the bottom, the temperature is adjusted by using the temperature control device, the water is absorbed by upper soil to keep the bottom of the feeding circumstance in a balance, which avoid uneven distribution of water in deep soil due to water supplements from surface of soil in prior art, and then influence larvae development;

(3) The depth of activity of *Hepialus* moth larvae in soil can be controlled by adjusting the soil temperature and moisture in the feeding device, the scope of activity of the larvae in infection phase can be controlled to move up, which increases contact between the larvae and the infecting device and then increases the infection rate of the larvae; and (4) Corresponding temperature and moisture are set at different stages of growth of *Hepialus* moth larvae to meet the growth requirements thereof, thus the quantity and quality of *Cordyceps* are increased significantly.

The cultivating *Cordyceps* system provided herein comprises the *Hepialus* moth trapping device, the *Hepialus* moth eggs screening device, the ascospores-collecting device, the mycelia-preparing device, the conidia-preparing device, the infection device and the feeding device, the interlocking and cooperation are between each device, each device plays on its own advantage and also provides a good basis for the next operation; due to the *Hepialus* moth trapping device, several technology difficulties met in capturing wild *Hepialus* moth in the wild are solved, and the separation efficiency and quality of *Hepialus* moth eggs are improved greatly through the *Hepialus* moth eggs screening device, both of above devices are used to ensure that the worms of *Cordyceps* come from the wild and have an excellent quality; collecting ascospores in the wild is achieved by the ascospores-collecting device, the collected ascospores have high vigor and original characteristics, which ensure the *Cordyceps* strain is of unadulterated varieties; the infection device and the feeding device are cooperating with each other, which can increase the hatch rate, infection rate, and survival rate of infected larvae, and thereby a high quantity and much larger of *Cordyceps* can be obtained, and the ingredients thereof are the same as those of wild *Cordyceps*; by using the above system, the technical difficulties of the enlargement and commercialization of *Cordyceps* production which always plagued people are solved, and the system makes an outstanding contribution to human health.

According to the second aspect of the present invention, provided herein is a method of using the system of cultivating *Cordyceps*, which comprises:

(1) trapping *Hepialus* moth and collecting *Hepialus* moth eggs by using the *Hepialus* moth trapping device;

(2) screening the *Hepialus* moth eggs collected in step (1) quantificationally by using the *Hepialus* moth eggs screening device to obtain matured *Hepialus* moth eggs;

(3) hatching the *Hepialus* moth eggs screened in step (2) by using the feeding device to obtain *Hepialus* moth larvae;

(4) collecting ascospores of *Cordyceps* by using the ascospores-collecting device to obtain *Cordyceps* ascospores;

(5) performing the liquid fermentation of the *Hirsutella sinensis* by using the mycelia-preparing device to obtain *Hirsutella sinensis* mycelia;

(6) performing the solid fermentation of the *Hirsutella sinensis* by using the conidia-preparing device to obtain *Hirsutella sinensis* conidia; and (7) loading the infecting device into the feeding device, and infecting the wild *Hepialus* moth larvae obtained in step (3), and feeding the infected wild *Hepialus* moth larvae to obtain *Cordyceps*; wherein the infecting device has infective liquid on it; and wherein the infective liquid contains *Cordyceps* ascospores, *Hirsutella sinensis* conidia and *Hirsutella sinensis* mycelia.

In some embodiments, the *Hepialus* moth eggs are hatched at 15±1° C. in step (3) by using the feeding device to obtain *Hepialus* moth larvae.

In some embodiments, the infective liquid in step (7) contains 60 to 70 *Cordyceps* ascospores per mL, 30 to 40 *Hirsutella sinensis* conidia per mL and 0.4 mg to 0.5 mg of *Hirsutella sinensis* mycelia per mL. The infecting device cooperating with the feeding device can improve the infecting ability of the infective liquid to *Hepialus* moth larvae, the infection rate can reach about 90%, thus the quantity and quality of *Cordyceps* are increased significantly.

In some embodiments, the *Hepialus* moth trapping device of step (1) and the ascospores-collecting device of step (4) trap and collect wild *Hepialus* moth and ascospores of wild *Cordyceps*.

The method of cultivating *Cordyceps* provided herein is suitable for industrial production due to mechanization of the whole process and operations with less manual intervention. Otherwise, a low infection rate has always been the key technical problem which restricts the scale production of *Cordyceps*. After a long term in depth research of cultivating *Cordyceps*, the inventors discovered that the infective liquid formed by mixing *Cordyceps* ascospores, conidia and mycelia in a specific proportion can significantly increase the infection rate of *Hepialus* moth larvae. By combining with the system of cultivating *Cordyceps* provided herein, the infection rate can be increased up to more than 90%, thereby the yield of *Cordyceps* is ensured, and the yield of *Cordyceps* cultivated by using the method disclosed herein is stabilized, the quality thereof is basically the same as wild *Cordyceps*.

REFERENCE SYMBOLS OF THE DRAWINGS

Figure 1:
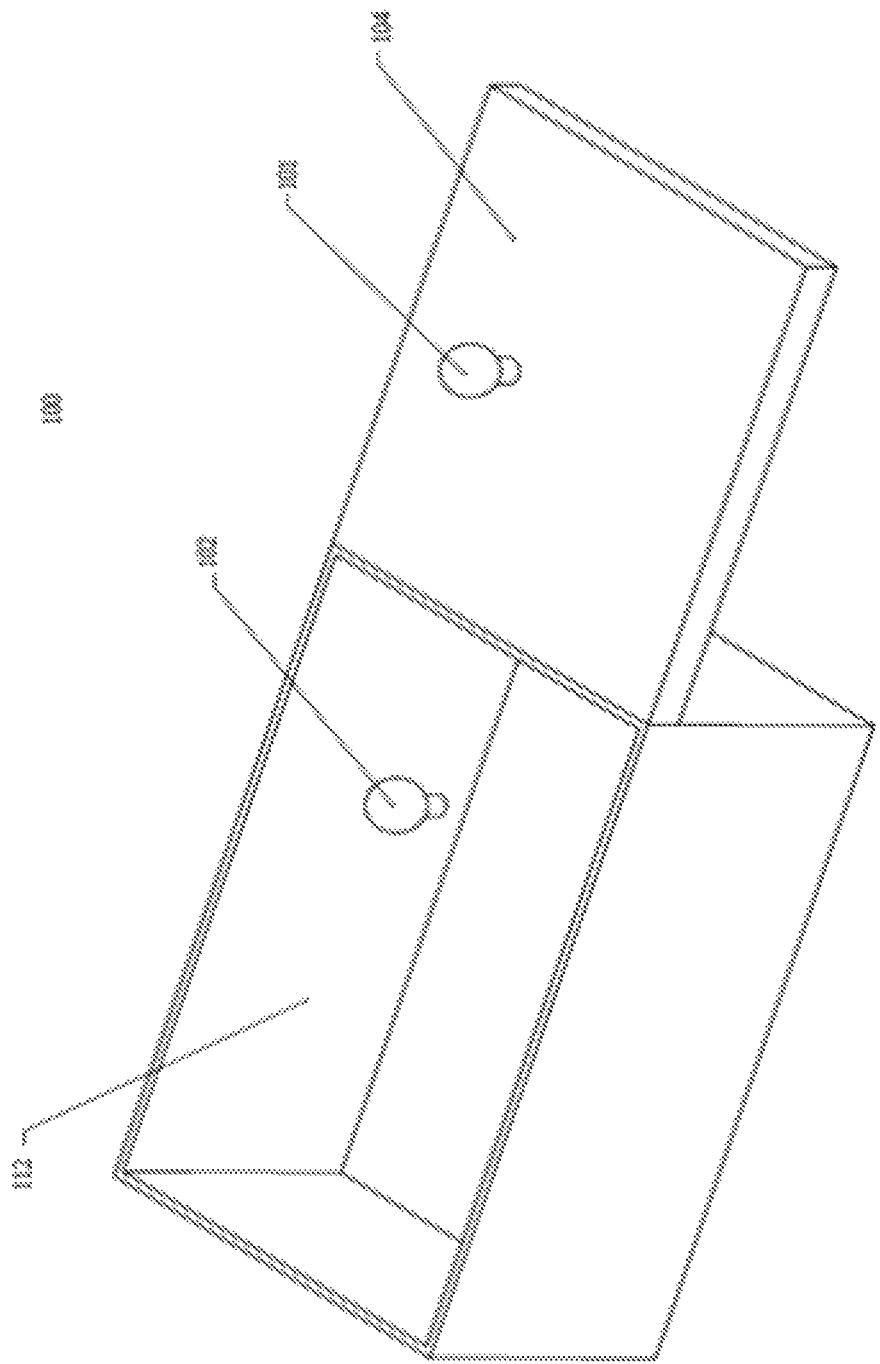
FIG. 1 depicts a diagram of a *Hepialus* moth trapping device according to an example of the invention.

100: a *Hepialus* moth trapping device; 101: a black light lamp; 102: a first red light lamp; 103: a second red light lamp; 104: a moth trapping platform; 105: a LED blue light lamp; 106: a rainproof shelter; 107: a *Hepialus* moth eggs collecting groove; 108: a visor; 109: a partition; 110: a controller; 111: a drainage hole; 112: a first body; 113: a *Hepialus* moth crawling board; 114: a *Hepialus* moth trapping area; 115: a *Hepialus* moth ovipositing area;

200: a *Hepialus* moth eggs screening device; 201: a pouring eggs device; 202: a flicking eggs device; 203: a dispersing box; 204: a dropping channel; 205: an immature eggs collecting device; 206: a mature eggs collecting device; 207: an eggs hole; 208: an extra small eggs collecting device; 209: a color sensor; 210: a gas valve; 211: a counter; 212: a selecting channel; 213: an extra small eggs hole; 214: a sub-selecting channel;

300: an ascospores-collecting device; 301: a barrel; 302: a closable opening; 303: a cover panel; 304: a turnable shaft; 305: a wind-power collecting device; 306: a fan; 307: a frame;

400: an infecting device; 401: a raised portion; 402: a mesh frame;

500: a feeding device; 501: a second device; 502: a sub pipeline; 503: a collective pipeline; 504: temperature control device; 505: a water inlet; 506: a water outlet.

EXAMPLES

The embodiments of the invention are described in detail below, a typical example of the embodiments is shown in accompanying drawings, wherein the same or similar symbols represent the same or similar elements or elements having the same or similar function. The embodiment described below by reference to the accompanying drawings is a typical example, which serves only for illustrative purpose, and is not a limitation of the invention.

In one aspect, the present invention provides a system of cultivating *Cordyceps*, which is described below by reference to FIGS. 1 to 6 according to one example of the invention. The system provided herein comprises a *Hepialus* moth trapping device 100, wherein the *Hepialus* moth trapping device 100 is used for trapping *Hepialus* moth and collecting *Hepialus* moth eggs; a *Hepialus* moth eggs screening device 200, wherein the *Hepialus* moth eggs screening device 200 is connected with the *Hepialus* moth trapping device 100; and wherein the *Hepialus* moth eggs screening device 200 is used for screening the *Hepialus* moth eggs automatically and collecting the screened *Hepialus* moth eggs quantificationally; an ascospores-collecting device 300, wherein the ascospores-collecting device 300 is used for collecting ascospores of *Cordyceps*; a mycelia-preparing device, wherein the mycelia-preparing device is used in liquid fermentation of *Hirsutella sinensis* to obtain mycelia thereof; a conidia-preparing device, wherein the conidia-preparing device is used in solid fermentation of *Hirsutella sinensis* to obtain conidia thereof; an infection device 400, wherein the infection device 400 is connected with the ascospores-collecting device 300, the mycelia-preparing device and the conidia-preparing device; and wherein the infection device 400 is used for infecting *Hepialus* moth larvae with infective liquid; and a feeding device 500, wherein the feeding device 500 is connected with the *Hepialus* moth eggs screening device 200 and the infecting device 400; and wherein the feeding device 500 is used for incubating the screened *Hepialus* moth eggs and incubating the infection *Hepialus* moth larvae to obtain *Cordyceps*.

According to the specific examples of the invention, as shown in FIG. 1, the *Hepialus* moth trapping device 100 comprises a first body 112, wherein a *Hepialus* moth trapping space is limited in the first body 112, and the bottom of the first body 112 is closed; a moth trapping platform 104, wherein the moth trapping platform 104 is installed outside the first body 112; a black light lamp 101, wherein the black light lamp 101 is installed over the moth trapping platform 104; a first red lamp 102, the first red lamp 102 is installed inside the *Hepialus* moth trapping space.

According to another example of the invention, the bottom of the first body 112 can be open.

In order to facilitate understanding, provided herein is a method of using the above *Hepialus* moth trapping device 100, specifically as follows: installing the *Hepialus* moth trapping device 100 in the *Hepialus* moth breeding base of the Qinghai-Tibet Plateau; installing gauzes around the first body 112, wherein the gauze is used for attaching *Hepialus* moth, and the top surface of the first body 112 is open, the around herein means the front surface, the back surface, the left surface, the right surface; turning the black light lamp 101 and the first red light lamp 102 on at 18 o'clock, the black light lamp 101 and the first red light lamp 102 flash alternately, the black light lamp flashes for 15 seconds each time, *Hepialus* moths and other flying insects are attracted to the moth trapping platform 104, and then the first red light lamp 102 flashes for 30 seconds each time, only *Hepialus* moths are attracted by the red light, and *Hepialus* moths are attracted specifically to the *Hepialus* moths trapping space, thus a large number of male and female *Hepialus* moths mate therein, and *Hepialus* moth eggs are collected at the bottom of the *Hepialus* moths trapping space.

According to the specific examples of the invention, the wavelengths of the black light lamp 101 of the *Hepialus* moth trapping device 100 is about 350 nm, the wavelengths of the first red light lamp 102 is about 620 nm. Thereby, a large number of male and female *Hepialus* moths can be attracted specifically to mate, and a large number of high quality *Hepialus* moth eggs can be obtained, and the yield and quality of *Hepialus* moth eggs are further increased.

Figure 2:
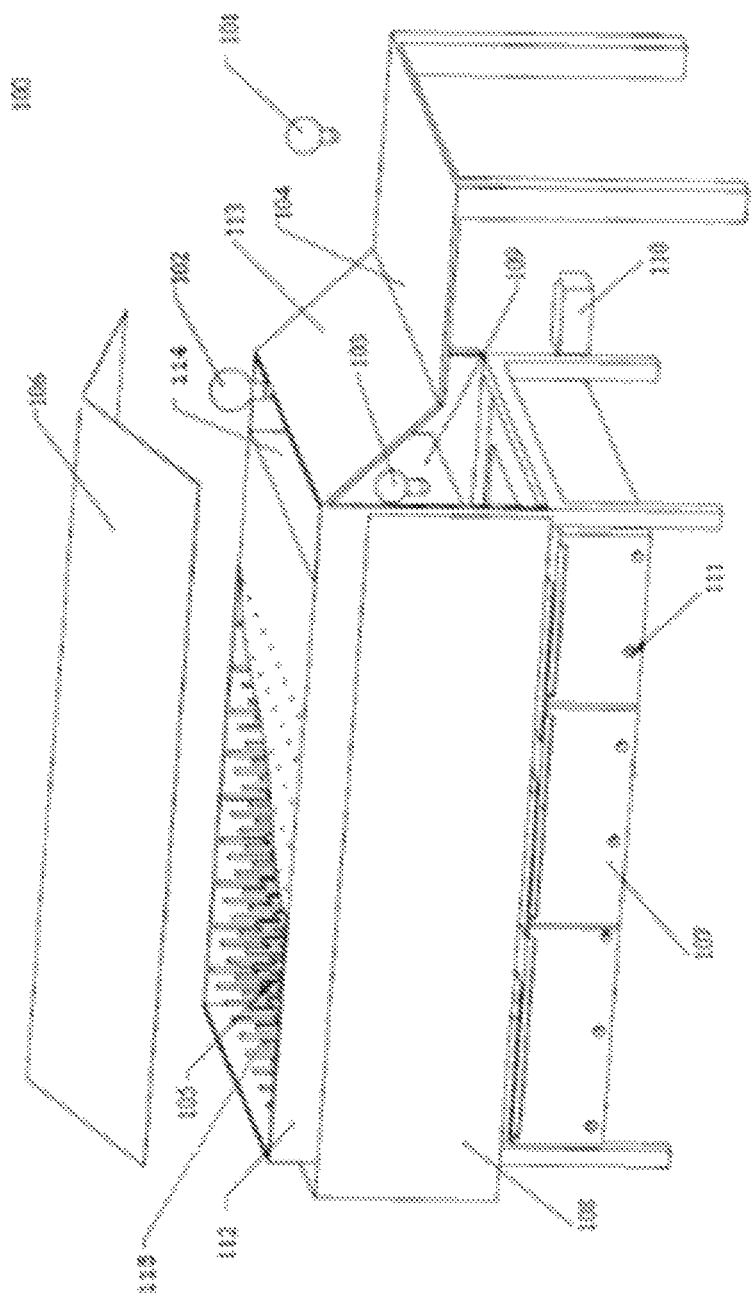
FIG. 2 depicts a diagram of a *Hepialus* moth trapping device according to another example of the invention.

According to the specific examples of the invention, as shown in FIG. 2, the *Hepialus* moth trapping device 100 comprises: a first body 112, a *Hepialus* moth trapping space is limited in the first body 112, the bottom and the right surface of the first body 112 are open; a visor 108, wherein the visors 108 are installed at the front surface, the rear surface and the left surface of the first body 112; a partition 109, wherein the partition 109 is installed inside of the first body 112, and divides the *Hepialus* moth trapping space into a *Hepialus* moth ovipositing area 115 and a *Hepialus* moth trapping area 114, and the *Hepialus* moth ovipositing area 115 and the *Hepialus* moth trapping area 114 open to each other at the bottom of the partition; a moth trapping platform 104, wherein the moth trapping platform 104 is installed outside the first body 112, and wherein the moth trapping platform is connected with the *Hepialus* moth trapping area through the *Hepialus* moth crawling board 113; a black light lamp 101, the black light lamp 101 is installed over the moth trapping platform 104; a first red lamp 102, wherein the first red lamp 102 is installed over the junction of the *Hepialus* moth crawling board 113 and the *Hepialus* moth trapping area 114; a second red lamp 103, wherein the second red light lamp 103 is installed at the junction of the *Hepialus* moth trapping area and the *Hepialus* moth ovipositing area at the bottom of the partition; one or more LED blue light lamps 105, wherein the LED blue light lamp 105 is installed in the *Hepialus* moth ovipositing area; a *Hepialus* moth eggs collecting groove 107, wherein the *Hepialus* moth eggs collecting groove 107 is installed under the first body 112; a rainproof shelter 106, wherein the rainproof shelter 106 is installed over the first body 112; a controller 110, wherein the controller 110 is connected with the black light lamp 101 and the first red light lamp 102, the second red light lamp 103 and the LED blue light lamps 105; a drainage hole 111, the drainage hole 111 is installed on the *Hepialus* moth eggs collecting groove 107.

According to another example of the invention, the right surface of the first body 112 can be closed.

In order to facilitate understanding, provided herein is a method of using the above *Hepialus* moth trapping device 100, specifically as follows: installing the *Hepialus* moth trapping device 100 in the *Hepialus* moth breeding base of the Qinghai-Tibet Plateau; installing gauzes around inside of the first body 112 and the bottom, and the top surface and the right surface of the first body 112 is uncovered with gauzes, the gauze is used for attaching *Hepialus* moth; turning the controller on at 18 o'clock, setting up a program bright and dim light of the lamp, the black light lamp 101, the first red light lamp 102 and the second red light lamp 103 flash alternately, the black light lamp flashes for 15 seconds each time, *Hepialus* moths and other flying insects are attracted to the moth trapping platform 104, and then the first red light lamp 102 and the second red light lamp 103 flashes for 30 seconds each time, only *Hepialus* moths are attracted by the red light, and *Hepialus* moths are attracted specifically to the *Hepialus* moths trapping area, and then the *Hepialus* moths are further attracted to the *Hepialus* moth ovipositing area under LED blue light lamp 105, thus a large number of male and female *Hepialus* moths mate therein, and *Hepialus* moth eggs are collected in the *Hepialus* moth eggs collecting groove 107.

According to the specific examples of the invention, the wavelengths of the black light lamp 101 of the *Hepialus* moth trapping device 100 is about 350 nm, the wavelengths of the first red light lamp 102 and the second red light lamp 103 are about 620 nm; the LED blue light lamp 105 has an illumination of 30 lux. Thereby, a large number of male and female *Hepialus* moths can be attracted specifically to mate, and a large number of high quality *Hepialus* moth eggs can be obtained, and the yield and quality of *Hepialus* moth eggs are further increased.

Figure 3:
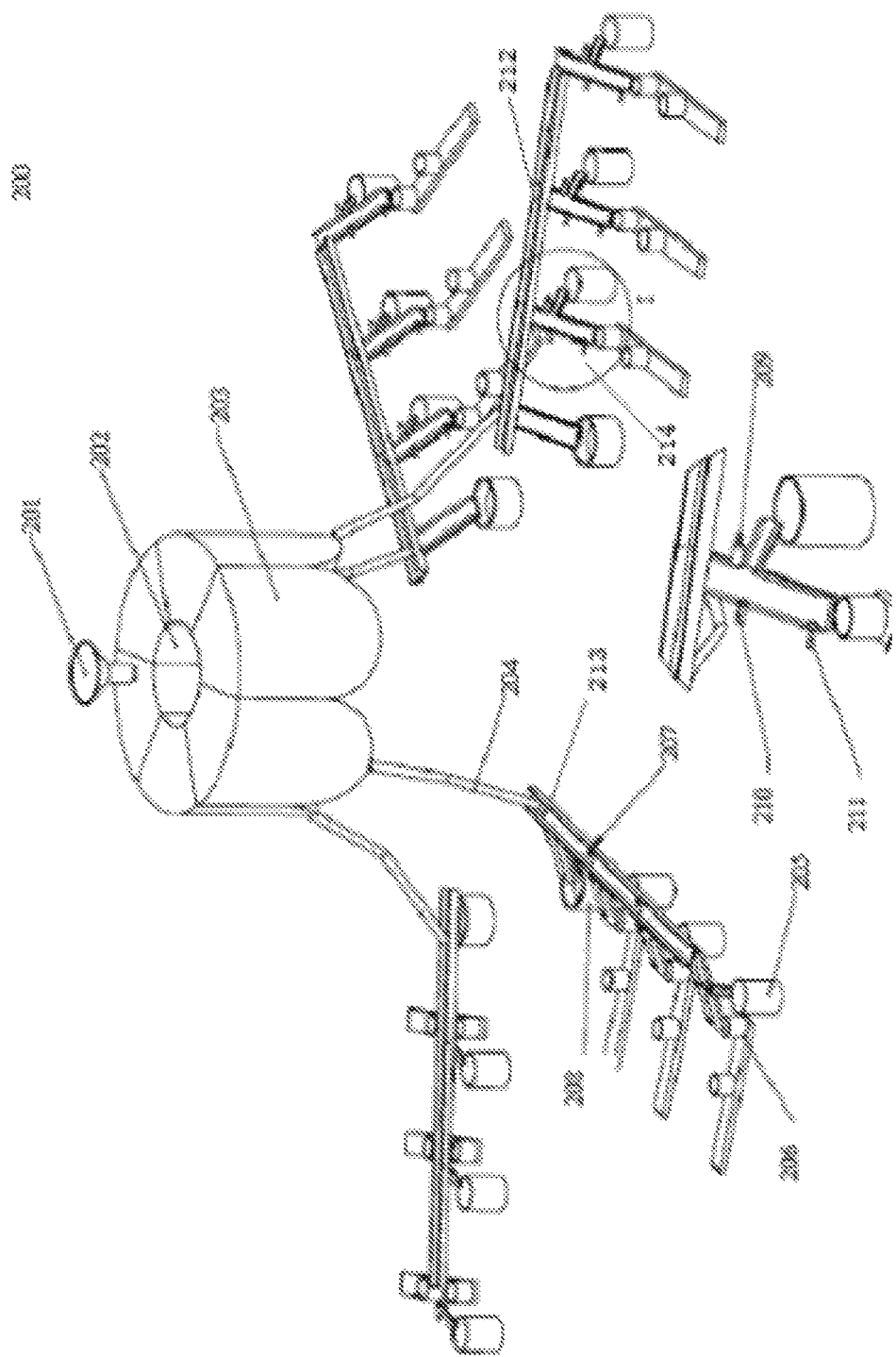
FIG. 3 depicts a diagram of a *Hepialus* moth eggs screening device according to an example of the invention.

According to the specific examples of the invention, as shown in FIG. 3, the *Hepialus* moth eggs screening device 200 comprises: a pouring eggs device 201, optionally, the pouring eggs device 201 is funnel-shaped; a dispersing box 203, wherein the dispersing box 203 comprises multiple dispersing grids; a flicking eggs device 202, wherein the flicking eggs device 202 is installed in the center of the multiple dispersing grids, and the flicking eggs device 202 is connected with the pouring eggs device 201, the *Hepialus* moth eggs are flicked to the multiple dispersing grids by the flicking eggs device 202; a dropping channel 204, wherein the dropping channel 204 is connected with the dispersing box 203 at one end; a selecting channel 212, wherein the selecting channel 212 is connected at the other end of the dropping channel 204; a extra small eggs hole 213 is set up on the selecting channel; an extra small eggs collecting device 208, wherein the extra small eggs collecting device 208 is connected to the extra small eggs hole 213; an eggs hole 207, wherein the eggs hole 207 is setup on the selecting channel and located downstream from the extra small eggs hole 213, and wherein the bore diameter of the eggs hole 207 is larger than that of the extra small eggs hole 213; multiple sub-selecting channels 214, wherein the sub-selecting channel 214 is connected with selecting channel 212 through the eggs hole 207; a color sensor 209, wherein the color sensor 209 is set up on the sub-selecting channel 214 and located downstream from the eggs hole 207; a gas valve 210, wherein the gas valve 210 is set up on the sub-selecting channel 214 and located downstream from the color sensor 209, and the gas valve 210 is used for blowing immature eggs away; an immature eggs collecting device 205, wherein the immature eggs collecting device 205 is installed at a side opposite to the gas valve 210, which is used for collecting developmental retardation and immature eggs; a counter 211, wherein the counter 211 is set up on the selecting channel 214 and located downstream from the gas valve 210; a mature eggs collecting device 206, wherein the mature eggs collecting device 206 is located on the sub-selecting channel 214 at the far end from the selecting channel 212, and the matured eggs collecting device 206 is used for collecting matured *Hepialus* moth eggs.

According to one specific example of the invention, the extra small eggs hole 213 and/or the eggs hole 207 may be one or multiple, and the bore diameter of the extra small eggs hole 213 and/or the eggs hole 207 may be adjusted according to the actual requirements, preferably, the bore diameter of the extra small eggs hole 213 is 0.55±0.1 mm; the bore diameter of the eggs hole 207 is 1.2±0.2 mm.

In order to facilitate understanding, provided herein is a method of using the *Hepialus* moth eggs screening device 200, specifically as follows: the obtained *Hepialus* moth eggs are poured into the flicking eggs device 202 by the pouring eggs device 201; the *Hepialus* moth eggs are flicked to the multiple dispersing grids of the dispersing box 203 by the flicking eggs device 202; the *Hepialus* moth eggs get into the dropping channel 204 across dispersing grids, and then get into the selecting channel 212; the bore diameter of the extra small eggs hole 213 is 0.55 mm, when the *Hepialus* moth eggs pass by the extra small eggs hole 213, the wild *Hepialus* moth eggs with the size of less than 0.55 mm across the extra small eggs hole and are collected in the extra small eggs collecting device 208, the other *Hepialus* moth eggs cross the multiple eggs holes 207 along the selecting channels get into the sub-selecting channels 214; the *Hepialus* moth eggs in the sub-selecting channels 214 are detected by the color sensor 209; if a sign of white or light color from the *Hepialus* moth eggs has been detected, the gas valve 210 is started, the immature *Hepialus* moth eggs are blown into the immature eggs collecting device 205, the mature *Hepialus* moth eggs pass through the counter 211 and get into the mature eggs collecting device 206.

Figure 4:
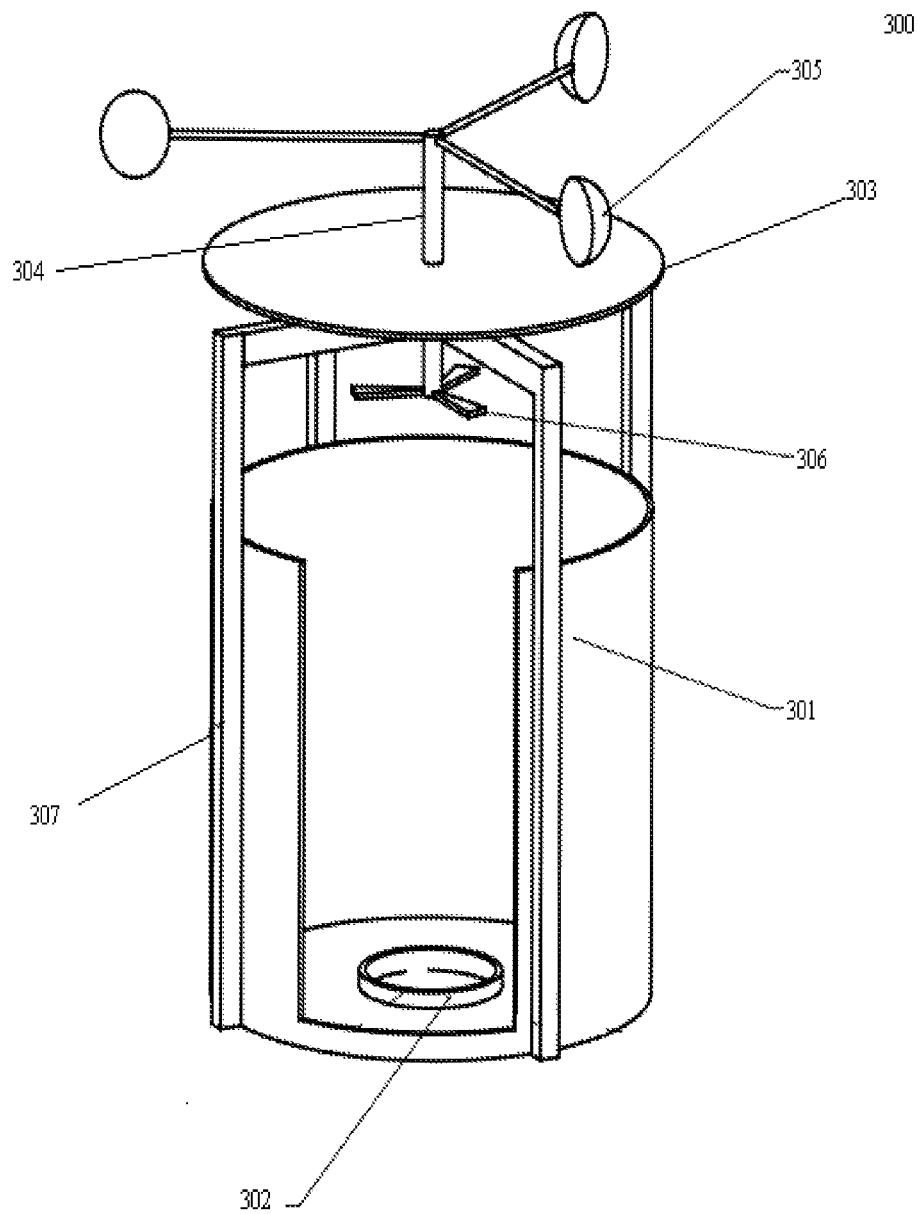
FIG. 4 depicts a diagram of an ascospores-collecting device according to an example of the invention.

According to the specific examples of the invention, as shown in FIG. 4, the ascospores-collecting device 300 comprises: a barrel 301, wherein an ascospores collecting space is limited in the barrel 301, wherein the barrel is made of transparent material, and wherein the barrel 301 has an open top; a closable opening 302, wherein the closable opening 302 is installed in the bottom of the barrel 301, and a protrusion of the closable opening 302 is higher than the bottom of the barrel 301, and the bottom of the barrel 301 can hold a protective liquid of ascospores; a cover panel 303, wherein the cover panel 303 is installed over the top of the barrel 301, and wherein the cover panel 303 is connected with the barrel 301 through a support 307; a turnable shaft 304, wherein the turnable shaft 304 passes through the cover panel 303; a wind-power collecting device 305, wherein the wind-power collecting device 305 is connected to the far end of the turnable shaft 304 from the barrel 301; and a fan 306, wherein the fan 306 is connected to the end of the turnable shaft 304 which is close to the barrel 301.

In order to facilitate understanding, provided herein is a method of using the ascospores-collecting device 300, specifically as follows: after leveling the field soil around an *Cordyceps*, the ascospores-collecting device 300 is put on the wild *Cordyceps*, and the fruiting body of the *Cordyceps* passes into the ascospores-collecting device 300 through the closable opening 302, the closable opening 302 is sealed with a semisolid low temperature wax and a protective liquid of ascospores is added into the bottom of the barrel 301. The sunshine shines through the transparent barrel 301 to the fruiting body of the *Cordyceps*, ascospores eject from the fruiting body when they are mature. The direction of wild wind is changed by the wind-power collecting device 305 and the fan 306, and the ascospores are blown into the protective liquid of ascospores in the bottom of the barrel 301, meanwhile the flowing air adjusts the internal temperature of the ascospores-collecting device 300, a too high temperature does not appear. The moisture of the fruiting body is kept through the natural evaporation of the protective liquid of ascospores, which avoids the fruiting body becomes withered.

Figure 5:
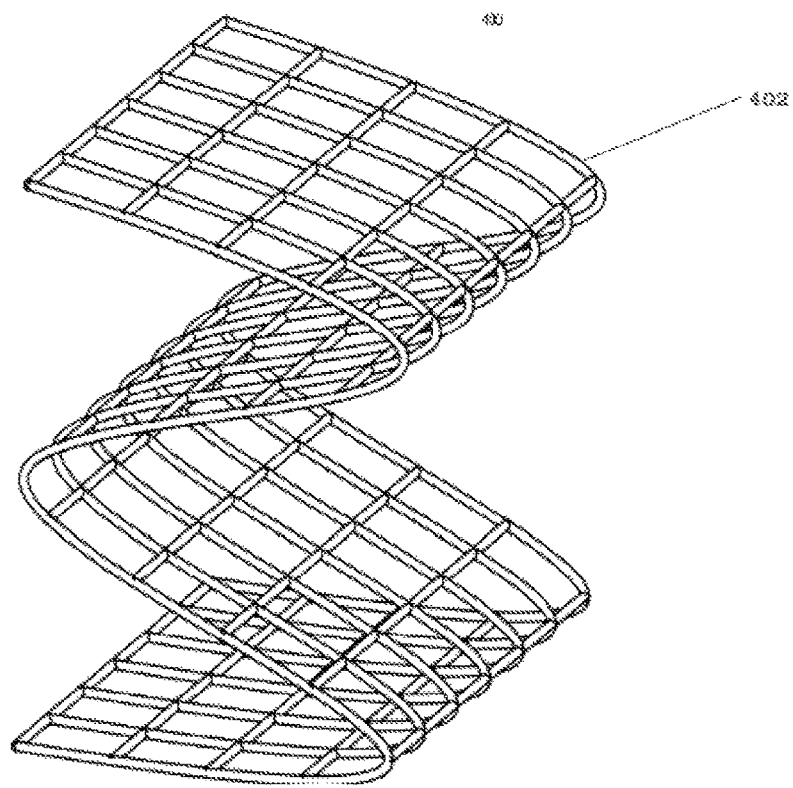
FIG. 5 depicts a diagram of an infecting device according to an example of the invention.
Figure 6:
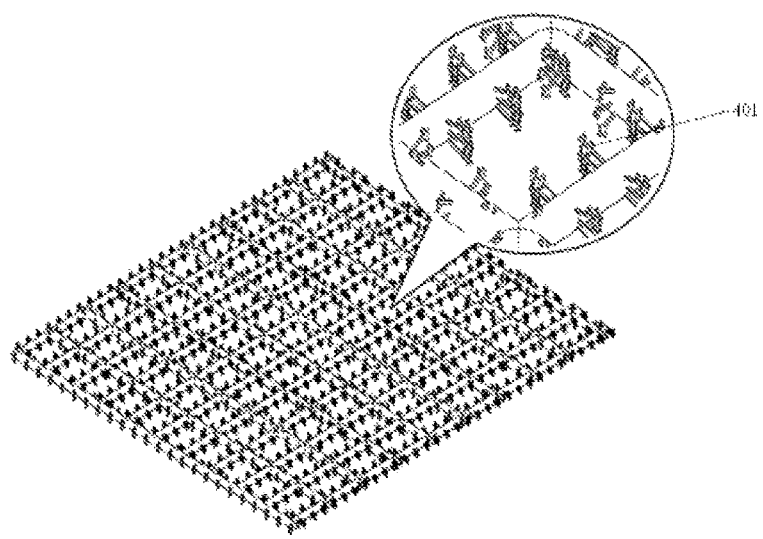
FIG. 6 depicts a partial enlargement of an infecting device according to an example of the invention.

According to the specific example of the invention, as shown in FIGS. 4 and 5, the infecting device comprises: a mesh frame 402; and one or more raised portions 401, wherein the raised portion 401 is formed on the mesh frame 402.

In order to facilitate understanding, provided herein is a method of using the infecting device 400, the infecting device 400 is dipped into an infective liquid for 24 h, the infective liquid is attached on the mesh frame 402 and the raised portion 401, and then the infection device 400 is taken out and dried at 18° C. in the shade for 24 h, and stored for later use. After hatching and culturing larvae for about 90 days, the infecting device 400 attached with infectious fungus is placed on the soil surface at the bottom of the feeding device 500, and then the fodder fit for third instar larvae is added, the fodder falls in the mesh frame of the infecting device 400, and the fodder surface is covered with soil. The larvae are forced to move up by adjusting the temperature control device 504 and the water compensating pipeline of the feeding device 500, the raised portion 401 can rub against the skin of the larvae, which promotes infection of the larvae with the infective liquid.

Figure 7:
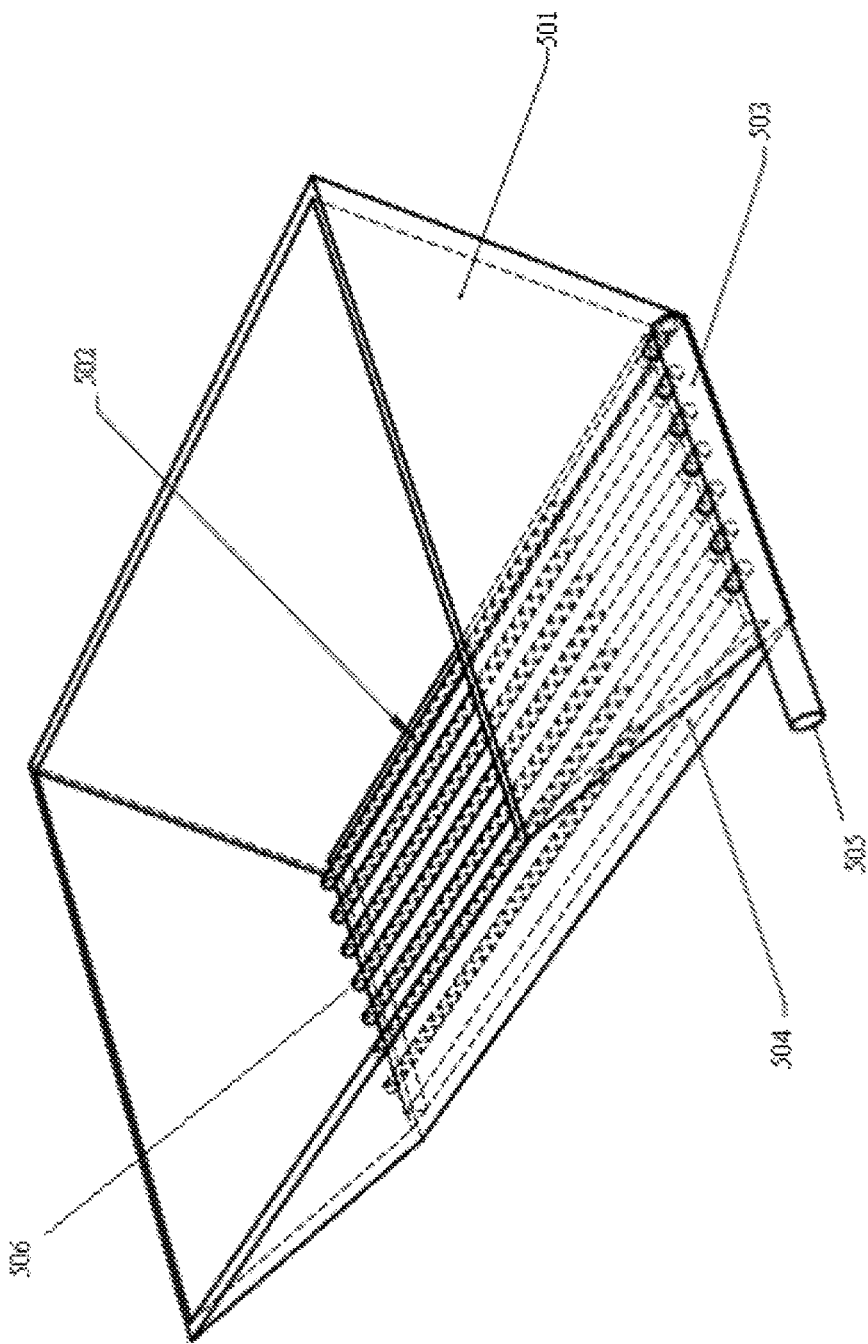
FIG. 7 depicts a diagram of an feeding device according to an example of the invention.

In some specific embodiments, as shown in FIG. 7, the feeding device 500 comprises a second body 501, wherein a feeding space is limited in the second body 501, and the cross sectional area of the feeding space is gradually increased from bottom to top; a water compensating pipeline, wherein the water compensating pipeline is installed at the bottom of the feeding space, wherein the water compensating pipeline comprises multiple sub pipelines 502 and one collective pipeline 503; wherein the collective pipeline 503 is connected with the sub pipeline 502, and wherein the collective pipeline 503 has a water inlet 505, and the sub pipeline 502 has a water outlet 506 and multiple water outlet holes on the wall; and a temperature control device 504, wherein the temperature control device 504 is installed at the bottom of the feeding space and used for controlling the temperature of the feeding space.

In order to facilitate understanding, provided herein is a method of using the feeding device 500, specifically as follows: soil and fodder are placed in the bottom of the feeding device 500; and then the screened *Hepialus* moth eggs are placed in the bottom of the feeding device 500; when it is required to supplement water to the feeding space, water crosses the water inlet 505 and enters into the collective pipeline 503, and then it is allotted to the sub pipeline 502 and gets into the feeding space through water outlet holes on the wall of the sub pipeline 502, the excess water is carried off through the water outlet 506 of the sub pipeline 502; adjusting the temperature and moisture of the feeding space by the water compensating pipeline and the temperature control device 504 to promote *Hepialus* moth eggs hatch into *Hepialus* moth larvae.

In another aspect, provided herein is a method of cultivating *Cordyceps* by using the above system of cultivating *Cordyceps*. In some specific embodiments, the method comprises:

(1) trapping *Hepialus* moth and collecting *Hepialus* moth eggs by using the *Hepialus* moth trapping device;

(2) screening the *Hepialus* moth eggs collected in step (1) quantificationally by using the *Hepialus* moth eggs screening device to obtain matured *Hepialus* moth eggs;

(3) hatching the *Hepialus* moth eggs screened in step (2) by using the feeding device to obtain *Hepialus* moth larvae;

(4) collecting ascospores of *Cordyceps* by using the ascospores-collecting device to obtain *Cordyceps* ascospores;

(5) performing the liquid fermentation of the *Hirsutella sinensis* by using the mycelia-preparing device to obtain *Hirsutella sinensis* mycelia;

(6) performing the solid fermentation of the *Hirsutella sinensis* by using the conidia-preparing device to obtain *Hirsutella sinensis* conidia; and (7) loading the infecting device into the feeding device, and infecting the wild *Hepialus* moth larvae obtained in step (3), and feeding the infection wild *Hepialus* moth larvae to obtain *Cordyceps*; wherein the infecting device has infective liquid on it; and wherein the infective liquid contains *Cordyceps* ascospores, *Hirsutella sinensis* conidia and *Hirsutella sinensis* mycelia.

The details of the method of cultivating *Cordyceps* by using the system of cultivating *Cordyceps* according to the specific embodiments are described below.

(1) Step of Trapping Wild *Hepialus* Moth and Collecting Wild *Hepialus* Moth Eggs by Using the *Hepialus* Moth Trapping Device According to the specific example of the invention, the *Hepialus* moth trapping device 100 is installed in the *Hepialus* moth breeding base of the Qinghai-Tibet Plateau; the controller 110 is turned on at 18 o'clock, a program to bright and dim light of the lamp is set up; the black light lamp 101, the first red light lamp 102 and the second red light lamp 103 flash alternately, the black light lamp 101 flashes for 15 seconds each time, *Hepialus* moths and other flying insects are attracted to the moth trapping platform 104, and then the first red light lamp 102 and the second red light lamp 103 flash for 30 seconds each time, only *Hepialus* moths are attracted by the red light, and *Hepialus* moths are attracted specifically to the *Hepialus* moths trapping area, and then the *Hepialus* moths are further attracted to the *Hepialus* moth ovipositing area under LED blue light lamp 105, thus a large number of male and female *Hepialus* moths mate therein, and *Hepialus* moth eggs are collected in the *Hepialus* moth eggs collecting groove 107.

(2) Step of Screening the Wild *Hepialus* Moth Eggs Quantificationally by Using the *Hepialus* Moth Eggs Screening Device to Obtain Matured *Hepialus* Moth Eggs According to the specific example of the invention, the obtained *Hepialus* moth eggs are poured into the flicking eggs device 202 by the pouring eggs device 201; the *Hepialus* moth eggs are flicked to the multiple dispersing grids of the dispersing box 203 by the flicking eggs device 202; the *Hepialus* moth eggs get into the dropping channel 204 across dispersing grids, and then get into the selecting channel 212; the bore diameter of the extra small eggs hole 213 is 0.55 mm, when the *Hepialus* moth eggs pass by the extra small eggs hole 213, the wild *Hepialus* moth eggs with the size of less than 0.55 mm cross the extra small eggs hole and are collected in extra small eggs collecting device 208, the other *Hepialus* moth eggs cross the multiple eggs holes 207 along the selecting channels get into the sub-selecting channels 214; the *Hepialus* moth eggs in the sub-selecting channels 214 are detected by the color sensor 209, if a sign of white or light color from the *Hepialus* moth eggs has been detected, the gas valve 210 is started, the immature *Hepialus* moth eggs are blown into the immature eggs collecting device 205; the mature *Hepialus* moth eggs pass through the counter 211 and get into the mature eggs collecting device 206.

(3) Step of Hatching the Screened *Hepialus* Moth Eggs by Using the Feeding Device to Obtain Wild *Hepialus* Moth Larvae According to the specific example of the invention, soil and fodder are placed in the bottom of the feeding device 500; and then the screened *Hepialus* moth eggs are placed in the bottom of the feeding device 500; the temperature and moisture of the feeding space are adjusted by the water compensating pipeline and the temperature control device to promote *Hepialus* moth eggs hatch into *Hepialus* moth larvae.

(4) Step of Collecting Ascospores of Wild *Cordyceps* by Using the Ascospores-Collecting Device to Obtain *Cordyceps* Ascospores According to the specific example of the invention, after leveling the field soil around an *Cordyceps*, the ascospores-collecting device 300 is put on the wild *Cordyceps*, and the fruiting body of the *Cordyceps* passes into the ascospores-collecting device 300 through the closable opening 302, the closable opening 302 is sealed with a semisolid low temperature wax and a protective liquid of ascospores is added into the bottom of the barrel 301. The sunshine shines through the transparent barrel 301 to the fruiting body of the *Cordyceps*, ascospores eject from the fruiting body when it is mature. The direction of wild wind is changed by the wind-power collecting device 305 and the fan 306, and the ascospores are blown into the protective liquid of ascospores in the bottom of the barrel 301, and meanwhile the flowing air adjusts the internal temperature of the ascospores-collecting device 300, a too high temperature does not appear. The moisture of the fruiting body is kept through the natural evaporation of the protective liquid of ascospores, which avoids the fruiting body become withered.

(5) Step of Performing the Liquid Fermentation of the *Hirsutella sinensis* by Using the Mycelia-Preparing Device to Obtain *Hirsutella sinensis* Mycelia According to the specific example of the invention, *Hirsutella sinensis* strains are seeded in a liquid shake flask and dark cultured at 18° C. for 10 d, when a large amount of mycelia have formed, the fungus liquid is stiff and not layered after standing, and a mycelia sample is stretched, colorless and separate clearly, and without autolysis, which is the terminal of fermentation, and the mycelia are diluted to a designated concentration.

(6) Step of Performing the Solid Fermentation of the *Hirsutella sinensis* by Using the Conidia-Preparing Device to Obtain *Hirsutella sinensis* Conidia According to the specific example of the invention, *Hirsutella sinensis* strains are seeded on a solid culture medium and dark cultured at 18° C. for 40 d, when mycelia are distributed on the whole culture medium surface, which are shifted to a 4° C. condition to carry out a low temperature stimulation, after 30 d, a large number of conidia are observed via microscopy. The mycelia and conidia are eluted, and purified through filtration and density gradient centrifugation to obtain pure conidia, which are diluted to a designated concentration.

(7) Step of Loading the Infecting Device into the Feeding Device, and Infecting the Wild *Hepialus* Moth Larvae Obtained in Step (3), and Feeding the Infection Wild *Hepialus* Moth Larvae to Obtain *Cordyceps*; Wherein the Infecting Device Contains Infective Liquid; the Infective Liquid Contains *Cordyceps* Ascospores, *Hirsutella sinensis* Conidia and *Hirsutella sinensis* Mycelia According to the specific example of the invention, the infecting device 400 is dipped into an infective liquid for 24 h, the infective solution is attached on the mesh frame 402 and the raised portion 401, and then the infection device 400 is taken out and dried at 18° C. in the shade for 24 h, and stored for later use. After hatching and culturing larvae for about 90 days, the infecting device attached with infectious fungus is placed on the soil surface in the bottom of the feeding device 500, and then the fodder fit for third instar larvae is added, the fodder falls in the mesh frame 402 of the infecting device, and the fodder surface is covered with soil. The larvae are forced to move up by adjusting the temperature control device 504 and the water compensating pipeline 503 of the feeding device 500, the raised portion 401 can rub against the skin of the larvae, which promotes infection of the larvae with the infective liquid.

According to the specific example of the present invention, the screened wild *Hepialus* moth eggs are hatched at 15±1° C. in step (3) by using the feeding device 500 to obtain *Hepialus* moth larvae.

According to the specific example of the present invention, the infective liquid in step (7) contains 60 to 70 *Cordyceps* ascospores per mL, 30 to 40 *Hirsutella sinensis* conidia per mL and 0.4 mg to 0.5 mg of *Hirsutella sinensis* mycelia per mL.

Example 1. The Preparation of Infective Liquid

The Preparation of Conidia:

*Hirsutella sinensis* strains were seeded on a solid culture medium and dark cultured at 18° C. for 40 d, when mycelia were distributed on the whole culture medium surface, which were shifted to a 4° C. condition to carry out a low temperature stimulation, after 30 d, a large number of conidia were observed via microscopy. The mycelia and conidia were eluted, and purified through filtration and density gradient centrifugation to obtain pure conidia, which were diluted to a designated concentration.

The Preparation of *Hirsutella sinensis* Mycelia:

*Hirsutella sinensis* strains were seeded in a liquid shake flask and dark cultured at 18° C. for 10 d, when a large amount of mycelia had formed, and the fungus liquid was stiff and not layered after standing, and a mycelia sample was stretched, colorless and separated clearly, and without autolysis, which was the terminal of fermentation, the fungus liquid was diluted to a designated concentration.

The Collection of *Cordyceps* Ascospores:

The ascospores-collecting device (as shown in FIG. 4) is adopted to collect ascospores of *Cordyceps* in the wild.

The physical differences between *Cordyceps* larvae induce the different infection time, and the larvae have different sensitivities to *Hirsutella sinensis* with different forms.

TABLE 1

| | Single-fungus infection | | | | |
|---|---|---|---|---|---|
| Ascospores | 40 particles/mL | 50 particles/mL | 60 particles/mL | 70 particles/mL | 80 particles/mL |
| Infection rate | 8.8% | 14.5% | 20.6% | 21.3% | 20.7% |
| Conidia | 10 particles/mL | 20 particles/mL | 30 particles/mL | 40 particles/mL | 50 particles/mL |
| Infection rate | 27.4% | 44.5% | 64.9% | 65.3% | 64.7% |
| Mycelia | 0.2 mg/mL | 0.3 mg/mL | 0.4 mg/mL | 0.5 mg/mL | 0.6 mg/mL |
| Infection rate | 25.3% | 32.7% | 41.2% | 41.8% | 41.6% |

TABLE 2

| Pairwise combinatorial infection | | |
|---|---|---|
| Ascospores | Conidia | Infection rate |
| 70 particles/mL | 40 particles/mL | 78.5% |
| 60 particles/mL | 30 particles/mL | 78.3% |
| 60 particles/mL | 20 particles/mL | 66.4% |
| 50 particles/mL | 30 particles/mL | 71.6% |
| Ascospores | Mycelia | Infection rate |
| 70 particles/mL | 0.5 mg/mL | 58.4% |
| 60 particles/mL | 0.4 mg/mL | 58.3% |
| 60 particles/mL | 0.3 mg/mL | 50.1% |
| 50 particles/mL | 0.4 mg/mL | 52.7% |
| Conidia | Mycelia | Infection rate |
| 40 particles/mL | 0.5 mg/mL | 81.8% |
| 30 particles/mL | 0.4 mg/mL | 82.3% |
| 30 particles/mL | 0.3 mg/mL | 74.2% |
| 20 particles/mL | 0.4 mg/mL | 62.9% |

TABLE 3

| Infection of three strains at the same time | | | |
|---|---|---|---|
| Ascospores | Conidia | Mycelia | Infection rate |
| 70 particles/mL | 40 particles/mL | 0.5 mg/mL | 89.7% |
| 60 particles/mL | 30 particles/mL | 0.4 mg/mL | 89.3% |
| 60 particles/mL | 30 particles/mL | 0.3 mg/mL | 84.6% |
| 60 particles/mL | 20 particles/mL | 0.4 mg/mL | 73.4% |
| 50 particles/mL | 30 particles/mL | 0.4 mg/mL | 85.7% |

The above experiment results show that the strains of *Cordyceps* infection comprise 60 to 70 *Cordyceps* ascospores per mL, 30 to 40 *Hirsutella sinensis* conidia per mL and 0.4 mg to 0.5 mg of *Hirsutella sinensis* mycelia per mL, which is the optimal combination and has a high infection rate.

TABLE 4

The optimal combination

| Ascospores | Conidia | Mycelia | Infection rate |
|---|---|---|---|
| 70 particles/mL | 40 particles/mL | 0.5 mg/mL | 89.7% |
| 60 particles/mL | 30 particles/mL | 0.4 mg/mL | 89.3% |

Example 2. The Method of Cultivating *Cordyceps*

Step 1. The *Hepialus* moth trapping device (as shown in FIG. 2) was installed at the *Hepialus* moth breeding base on the Tibetan plateau. The controller 110 was turned on at 18-21 o'clock, the program to bright and dim light of the lamp was set up, the black light lamp 101, the first red light lamp 102 and the second red light lamp 103 flashed alternately. The black light lamp 101 (350 nm) flashed for 15 seconds each time, *Hepialus* moths and other flying insects were attracted to the moth trapping platform 104, and then the first red light lamp 102 (620 nm) and the second red light lamp 103 (620 nm) flashed for 30 seconds each time, only *Hepialus* moths were attracted by the red light, and *Hepialus* moths were attracted specifically to the *Hepialus* moths trapping area, and then the *Hepialus* moths were further attracted to the *Hepialus* moth ovipositing area under LED blue light lamp 105, thus a large number of male and female *Hepialus* moths mate therein, and *Hepialus* moth eggs were collected in the *Hepialus* moth eggs collecting groove 107. In the morning, the dead moths were cleaned up and the *Hepialus* moth eggs were collected from the bottom of the collecting device.

Step 2. The collected *Hepialus* moth eggs were screened by using the *Hepialus* moth eggs screening device (as shown in FIG. 3) to screen out the wild *Hepialus* moth eggs with the diameter less than 0.55 mm and immature *Hepialus* moth eggs, and the maturate *Hepialus* moth eggs were collected quantificationally.

Step 3. When the *Cordyceps* at the *Hepialus* moth breeding base on the Tibetan plateau sent forth perithecia, the ascospores-collecting device (as shown in FIG. 3) was installed on the *Cordyceps*. After adding a protective liquid of ascospores, the ascospores were naturally mature, and the collection process was complete. After 20 days, the liquid was collected from the collecting device to obtain the ascospores liquid.

Step 4. *Hirsutella sinensis* strains were fermented to collect conidia and mycelia, by using a combination of 70 *Cordyceps* ascospores per mL, 40 *Hirsutella sinensis* conidia per mL and 0.5 mg of *Hirsutella sinensis* mycelia per mL, an infective liquid was prepared and stored.

Step 5. The infection device (as shown in FIG. 5) was dipped in the above infective liquid for 24 h, then taken out and placed at 18° C. in the shade to dry for 24 h, and then stored.

Step 6. The screened mature *Hepialus* moth eggs were placed in the bottom of the feeding device (as shown in FIG. 7), and covered with soil and fodder. The feeding device was placed in a clean area at 13° C. The heating equipment in the bottom of the feeding device controlled the temperature at 15° C.±1° C. to incubate eggs. After all the eggs hatched, the heating equipment was turned off. When the larvae were hatched out, and every day, after watering the bottom, the heating equipment was turned on, the temperature was kept at 14° C. for 2 h to balance the water.

Step 7. At about 90 days after the larvae were hatched out, the infection device (as shown in FIG. 5) attached with infection fungus was placed on the soil surface in the feeding device, and the fodder suitable for the subsequent third instar larvae was added and covered by the soil. The addition of water at the bottom was stopped, and the bottom was heated at 15° C. in order to lose water from the soil bottom, and the soil was watered form the top of the feeding device, which made the larvae to move up. After one month of infection, the soil was watered from the bottom again, and the bottom was heating to balance the water, the moisture of the bottom soil was controlled at 23% to 28%, the activity space of larvae was increased. When *Cordyceps* grew up, the *Cordyceps* was harvested.

The hatch rate of the choice *Hepialus* moth eggs approximates 100%, and the infection rate is high, the process of "from the larvae to formation of *Cordyceps*" is stable, the yield of *Cordyceps* reaches 90%.

Example 3. Detection of IR Fingerprint Spectra

20 Batches of wild *Cordyceps* from different sources (including Sichuan *Cordyceps* samples 6 batches, Tibet *Cordyceps* samples 7 batches, Qinghai *Cordyceps* samples 7 batches), 20 batches of the *Cordyceps* cultured according to the example 2 of the invention, and 4 Counterfeit *Cordyceps sinensis* (*Cordyceps sobolifera*, *Cordyceps militaris*, mycelium powder of *Hirsutella sinensis*, mycelium powder of *Paecilomyces Hepialus*) were analyzed by infrared fingerprint scan using preparation technique of solid sample (the method passed the examinations of methodology, including repeatability, accuracy, stability and specificity, and the results show that the detection method of *Cordyceps* IR fingerprint spectra used herein has good specificity and accuracy, which can be used for detecting *Cordyceps* IR fingerprint spectra).

The instruments include TENSOR27 infrared spectrometer (Bruker Corporation); CrushIR pressure machine (US PIKE Corporation); XP204 analytic balance (METTER Corporation). Potassium bromide, purchased from aladdin Corporation.

Figure 8:
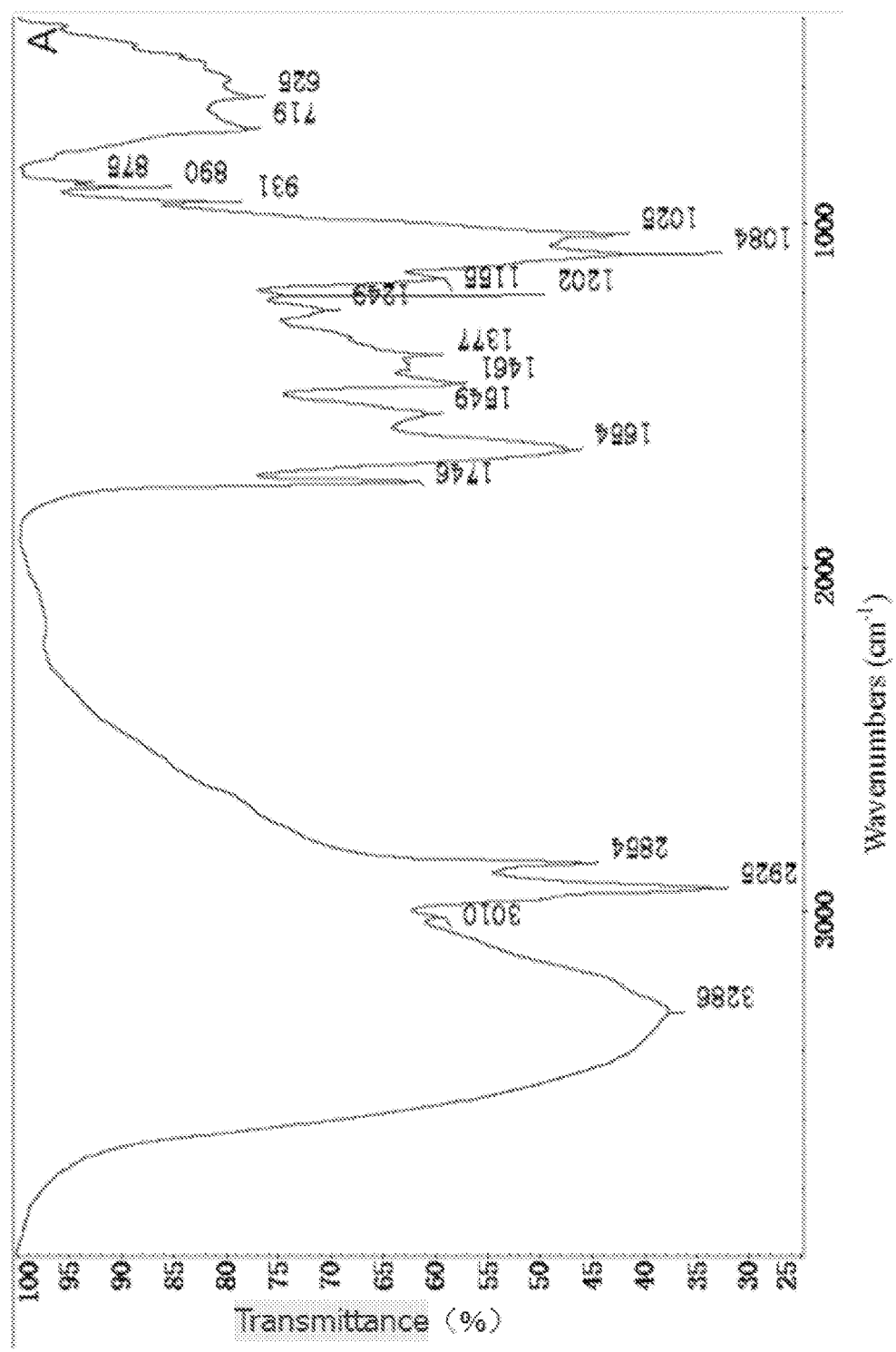
FIG. 8 depicts the standard IR fingerprint spectra of *Cordyceps* according to example 3 of the invention.
Figure 9:
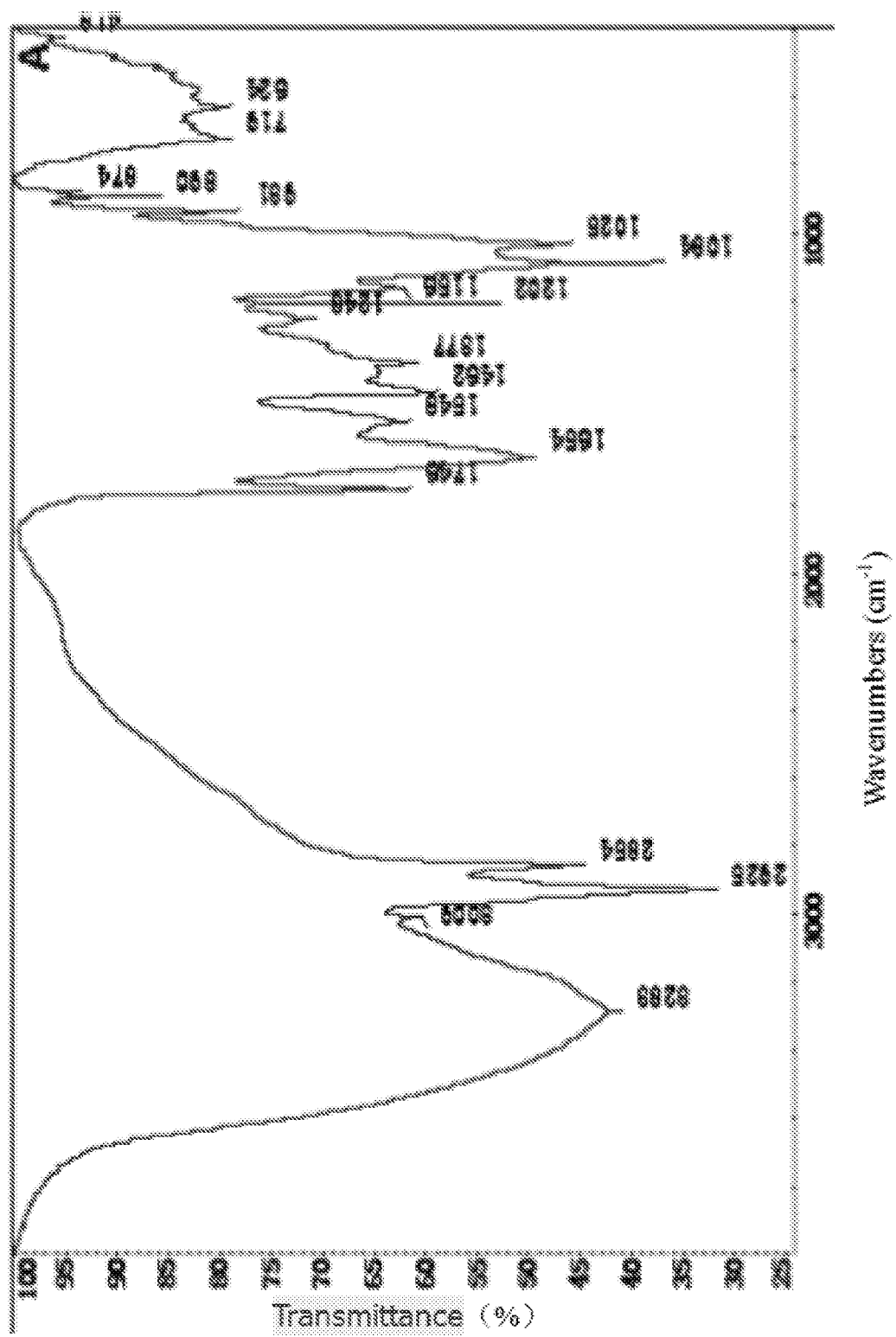
FIG. 9 depicts the IR fingerprint spectra of *Cordyceps* cultivated by the method of the invention according to example 3 of the invention.

Data processing: the original spectra of 20 batches of wild *Cordyceps* were processed via the OMNIC infrared software provided by Thermo Fisher Scientific Corporation to obtain the standard IR fingerprint spectra of *Cordyceps* (as shown in FIG. 7), and the IR fingerprint spectra of the *Cordyceps* cultivated by the method disclosed herein is shown in FIG. 8. The similarity between each sample and the standard IR fingerprint spectra of *Cordyceps* was calculated. The results are shown in the following table:

TABLE 5

The results of similarity of IR fingerprint spectra of *Cordyceps*

| The *Cordyceps* cultivated by the method disclosed herein | | Wild *Cordyceps* | | Counterfeit *cordyceps* | |
|---|---|---|---|---|---|
| Sample Number | Similarity | Sample Number | Similarity | Sample | Similarity |
| 1 | 0.9857 | 1 | 0.9525 | *Cordyceps sobolifera* | 0.8486 |
| 2 | 0.9771 | 2 | 0.9320 | *Cordyceps sinensis* flowers | 0.5855 |
| 3 | 0.9741 | 3 | 0.9673 | Mycelium powder of *Hirsutella sinensis* | 0.7989 |
| 4 | 0.9912 | 4 | 0.9576 | Mycelium powder of *paecilomyces Hepialus* moth | 0.7899 |
| 5 | 0.9817 | 5 | 0.9074 | — | — |
| 6 | 0.9853 | 6 | 0.9276 | — | — |
| 7 | 0.9858 | 7 | 0.9399 | — | — |
| 8 | 0.9895 | 8 | 0.9776 | — | — |
| 9 | 0.9966 | 9 | 0.9464 | — | — |
| 10 | 0.9946 | 10 | 0.9632 | — | — |
| 11 | 0.9959 | 11 | 0.9616 | — | — |
| 12 | 0.9882 | 12 | 0.9681 | — | — |
| 13 | 0.9829 | 13 | 0.9626 | — | — |
| 14 | 0.9836 | 14 | 0.9254 | — | — |
| 15 | 0.9959 | 15 | 0.9107 | — | — |
| 16 | 0.9890 | 16 | 0.9204 | — | — |
| 17 | 0.9926 | 17 | 0.9592 | — | — |
| 18 | 0.9850 | 18 | 0.9702 | — | — |
| 19 | 0.9820 | 19 | 0.9743 | — | — |
| 20 | 0.9876 | 20 | 0.9322 | — | — |

The similarity of *Cordyceps* cultivated by the method of example 2 reaches 0.990 and more, and the *Cordyceps* has little difference between each batch, which has the same quality with wild *Cordyceps*.

The process has advantages of operation with less manual intervention, steady production, suitability of industrial production.

In the description disclosed herein, it should be understood that, the terms "central", "longitudinal", "lateral", "length", "breadth", "thickness", "above", "below", "front", "rear", "left", "right", "vertical", "horizontal", "top", "bottom", "inner", "outer", "clockwise", "counter-clockwise", "axial", "radial", "circumference" and so on, should be construed to refer to the orientation as described or as shown in the drawings. These terms are merely for convenience and concision of description and do not alone indicate or imply that the device or element referred to must have a particular orientation. Thus, it cannot be understood to limit the present disclosure.

In addition, terms such as "first" and "second" are used herein for purposes of description and are not intended to indicate or imply relative importance or significance or impliedly indicate quantity of the technical feature referred to. Thus, the features limited by "first" and "second" are intended to indicate or imply including one or more than one these features. In the description disclosed herein, "multiple" means at least two, such as two, three, and the like, unless specified or limited otherwise.

In the present invention, unless specified or limited otherwise, the terms "mounted," "connected," "coupled," "fixed" and the like are used broadly, and may be, for example, fixed connections, detachable connections, or integral connections; may also be mechanical or electrical connections; may also be direct connections or indirect connections via intervening structures; may also be inner communications or interaction of two elements, unless specified or limited otherwise. The above terms can be understood by those skilled in the art according to specific situations.

In the present invention, unless specified or limited otherwise, a structure in which a first feature is "on" or "below" a second feature may include an embodiment in which the first feature is in direct contact with the second feature, and may also include an embodiment in which the first feature and the second feature are not in direct contact with each other, but are contacted via an additional feature formed therebetween. Furthermore, a first feature "on", "above", "over", or "on top of" a second feature may include an embodiment in which the first feature is right or obliquely "on", "above", "over", or "on top of" the second feature, or just means that the first feature is at a height higher than that of the second feature. While a first feature "below," "under," or "on/at/in bottom of" a second feature may include an embodiment in which the first feature is right or obliquely "below," "under," or "on/at/in bottom of" the second feature, or just means that the first feature is at a height lower than that of the second feature.

Reference throughout this specification to "an embodiment", "some embodiments", "one embodiment", "another example", "an example", "a specific examples", or "some examples", means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific examples", or "in some examples", in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A system of cultivating *Cordyceps*, characterized in that the system comprises:
   (a) a *Hepialus* moth trapping device, wherein the *Hepialus* moth trapping device traps *Hepialus* moth and collects *Hepialus* moth eggs;
   (b) a *Hepialus* moth eggs screening device, wherein the *Hepialus* moth eggs screening device is connected with the *Hepialus* moth trapping device; and wherein the *Hepialus* moth eggs screening device screens the *Hepialus* moth eggs automatically and collects the screened *Hepialus* moth eggs quantificationally;
   (c) an ascospores-collecting device, wherein the ascospores-collecting device collects ascospores of *Cordyceps*;
   (d) a mycelia-preparing device, wherein the mycelia-preparing device prepares mycelia by liquid fermentation of *Hirsutella sinensis*;
   (e) a conidia-preparing device, wherein the conidia-preparing device prepares conidia by solid fermentation of *Hirsutella sinensis*;
   (f) an infection device, wherein the infection device is connected with the ascospores-collecting device, the mycelia-preparing device and the conidia-preparing device; and wherein the infection device infects *Hepialus* moth larvae with infective liquid; and wherein the infective liquid contains *Cordyceps* ascospores, *Hirsutella sinensis* conidia and *Hirsutella sinensis* mycelia; and
   (g) a feeding device, wherein the feeding device is connected with the *Hepialus* moth eggs screening device and the infecting device; and wherein the feeding device incubates the screened *Hepialus* moth eggs and feeds the infected *Hepialus* moth larvae to obtain *Cordyceps*.

2. The system of claim 1, characterized in that the *Hepialus* moth trapping device comprises:
   (a) a first body, wherein a *Hepialus* moth trapping space is limited in the first body;
   (b) a moth trapping platform, wherein the moth trapping platform is installed outside the first body; and
   (c) a non-specific attracting light source and a specific attracting light source, wherein the non-specific attracting light source and the specific attracting light source are installed successively along the direction of the moth trapping platform to the *Hepialus* moth trapping space.

3. The system of claim 2, characterized in that the *Hepialus* moth trapping device further comprises:
   (d) a *Hepialus* moth crawling board, wherein the *Hepialus* moth crawling board is connected with the moth trapping platform at one end, the other end is connected with the first body;
   (e) the non-specific attracting light source is a black light lamp, wherein the black light lamp is installed over the moth trapping platform;
   (f) the specific attracting light source is a red light lamp, wherein the red light lamp is installed over the first body; and
   (g) a controller, wherein the controller is connected with the black light lamp and the red light lamp respectively; and wherein the controller controls the bright and dim light of each lamp.

4. The system of claim 3, characterized in that the first body comprises a partition inside, wherein the first body is divided by the partition into a *Hepialus* moth trapping area and a *Hepialus* moth ovipositing area, and wherein the *Hepialus* moth trapping area is connected with the moth trapping platform through the *Hepialus* moth crawling board, and the *Hepialus* moth trapping area and the *Hepialus* moth ovipositing area open to each other at the bottom of the partition.

5. The system of claim 4, characterized in that the red light lamp comprises a first red light lamp and a second red light lamp, wherein the first red light lamp is installed over the junction of the *Hepialus* moth crawling board and the *Hepialus* moth trapping area; and wherein the second red light lamp is installed at the junction of the *Hepialus* moth trapping area and the *Hepialus* moth ovipositing area at the bottom of the partition.

6. The system of claim 4, characterized in that the *Hepialus* moth trapping device further comprises one or more LED blue light lamps and an *Hepialus* moth eggs collecting groove, wherein the LED blue light lamp is installed in the *Hepialus* moth ovipositing area, the *Hepialus* moth eggs collecting groove is installed under the first body.

7. The system of claim 6, characterized in that the LED blue light lamp has an illumination of 25~35 lux.

8. The system of claim 1, characterized in that the *Hepialus* moth eggs screening device comprises:
   (a) a dispersing box;
   (b) one or more dropping channels, wherein the dropping channel is connected with the dispersing box at one end; and
   (c) one or more selecting channels, wherein the selecting channel is connected at the other end of the dropping channel, and wherein an extra small eggs hole, a color sensor, a gas valve and a mature eggs collecting device are setup on the selecting channel successively.

9. The system of claim 8, characterized in that the selecting channel further comprises:
   (a) an eggs hole, wherein the eggs hole is set up on the selecting channel and located downstream from the extra small eggs hole, and wherein the bore diameter of the eggs hole is larger than that of the extra small eggs hole;
   (b) multiple sub-selecting channels, wherein the sub-selecting channels are connected with selecting channel through the eggs hole;
   (c) the color sensor is set up on the sub-selecting channel and located downstream from the eggs hole;
   (d) the gas valve is set up on the sub-selecting channel and located downstream from the color sensor, and the gas valve blows immature eggs away; and
   (e) the mature eggs collecting device is located on the sub-selecting channel at the far end from the selecting channel, and the matured eggs collecting device collects matured *Hepialus* moth eggs.

10. The system of claim 9, characterized in that the selecting channel and the sub-selecting channel are set up obliquely.

11. The system of claim 8, characterized in that the dispersing box comprises multiple dispersing grids, wherein the dispersing grids are connected with dropping channel, and the dropping channel is set up obliquely.

12. The system of any one of claim 8, characterized in that the *Hepialus* moth eggs screening device further comprises a counter, wherein the counter is set up on the selecting channel and located downstream from the gas valve.

13. The system of claim 1, characterized in that the ascospores-collecting device comprises:
   (a) a barrel, wherein an ascospores collecting space is limited in the barrel, wherein the barrel is made of transparent material, and wherein the barrel has an open top;
   (b) a closable opening, wherein the closable opening is installed in the bottom of the barrel;
   (c) a cover panel, wherein the cover panel is installed over the top of the barrel, and wherein the cover panel is connected with the barrel through a support;
   (d) a turnable shaft, wherein the turnable shaft passes through the cover panel;
   (e) a wind-power collecting device, wherein the wind-power collecting device is connected to the far end of the turnable shaft from the barrel; and
   (f) a fan, wherein the fan is connected to the other end of the turnable shaft which is close to the barrel.

14. The system of claim 1, characterized in that the infecting device comprises:
   (a) a mesh frame; and
   (b) one or more raised portions, wherein the raised portion is formed on the mesh frame.

15. The system of claim 1, characterized in that the feeding device comprises:
   (a) a second body, wherein a feeding space is limited in the second body;
   (b) a water compensating pipeline, wherein the water compensating pipeline is installed at the bottom of the feeding space, wherein the water compensating pipeline comprises one collective pipeline and multiple sub pipelines; wherein the collective pipeline is connected with the sub pipeline, and wherein the collective pipeline has a water inlet, and the sub pipeline has a water outlet and multiple water outlet holes on the wall; and
   (c) a temperature control device, wherein the temperature control device is installed at the bottom of the feeding space, and wherein the temperature control device controls the temperature of the feeding space.

16. A method of cultivating *Cordyceps* according to the system of claim 1, characterized in that the method comprises the steps of:
   (1) trapping *Hepialus* moth and collecting *Hepialus* moth eggs by using the *Hepialus* moth trapping device;
   (2) screening the *Hepialus* moth eggs collected in step (1) quantificationally by using the *Hepialus* moth eggs screening device to obtain matured *Hepialus* moth eggs;
   (3) hatching the *Hepialus* moth eggs screened in step (2) by using the feeding device to obtain *Hepialus* moth larvae;
   (4) collecting ascospores of *Cordyceps* by using the ascospores-collecting device to obtain *Cordyceps* ascospores;
   (5) performing the liquid fermentation of the *Hirsutella sinensis* by using the mycelia-preparing device to obtain *Hirsutella sinensis* mycelia;
   (6) performing the solid fermentation of the *Hirsutella sinensis* by using the conidia-preparing device to obtain *Hirsutella sinensis* conidia; and
   (7) loading the infecting device into the feeding device; and infecting the wild *Hepialus* moth larvae obtained in step (3); and feeding the infected wild *Hepialus* moth larvae to obtain *Cordyceps*; wherein the infecting device has infective liquid on it; and wherein the infective liquid contains *Cordyceps* ascospores, *Hirsutella sinensis* conidia and *Hirsutella sinensis* mycelia.

17. The method of claim 16, characterized in that hatching the *Hepialus* moth eggs at 15±1° C. in step (3) by using the feeding device to obtain *Hepialus* moth larvae.

18. The method of claim 16, characterized in that the infective liquid contains 60 to 70 *Cordyceps* ascospores per mL, 30 to 40 *Hirsutella sinensis* conidia per mL and 0.4 mg to 0.5 mg of *Hirsutella sinensis* mycelia per mL.

* * * * *